United States Patent
Nicolle et al.

[11] Patent Number: 6,162,394
[45] Date of Patent: *Dec. 19, 2000

[54] HYGIENIC AGENT FOR USE IN HEMODIALYSIS

[75] Inventors: Rémy Nicolle; Eric Jourdan-Laforte, both of Paris, France

[73] Assignee: L'Air Liquide, Societe Anonyme pour l'Etude et l'Exploitation des Procedes Georges Claude, Paris, Cedex, France

[*] Notice: This patent is subject to a terminal disclaimer.

[21] Appl. No.: 09/187,758

[22] Filed: Nov. 9, 1998

Related U.S. Application Data

[62] Division of application No. 08/389,971, Feb. 16, 1995, Pat. No. 5,851,483, which is a continuation of application No. 08/111,966, Aug. 26, 1993, abandoned, which is a continuation of application No. 07/653,972, Feb. 11, 1991, abandoned, which is a continuation of application No. 07/438,293, Nov. 20, 1989, abandoned.

[30] Foreign Application Priority Data

Nov. 23, 1988 [FR] France ................................ 88 15252

[51] Int. Cl.⁷ .............................. A61M 1/14; A61M 1/34; A61M 1/36

[52] U.S. Cl. ............................... 422/28; 422/29; 422/44; 424/616

[58] Field of Search .................. 422/28, 44, 29; 424/613, 616

[56] References Cited

U.S. PATENT DOCUMENTS

| | | |
|---|---|---|
| 4,209,402 | 6/1980 | Gentles . |
| 4,444,597 | 4/1984 | Gortz et al. . |
| 4,552,721 | 11/1985 | Fentress et al. . |
| 4,587,264 | 5/1986 | Jourdan-Laforte et al. . |
| 4,680,163 | 7/1987 | Blidschun et al. . |
| 4,690,772 | 9/1987 | Tell et al. . |
| 4,695,385 | 9/1987 | Boag . |
| 4,743,447 | 5/1988 | Le Rouzic et al. . |
| 5,851,483 | 12/1998 | Nicolle et al. . |

FOREIGN PATENT DOCUMENTS

| | | |
|---|---|---|
| 0 193 416 | 9/1986 | European Pat. Off. . |
| 2584503 | 1/1987 | France . |
| 96833 | 5/1972 | Germany . |
| 2623917 | 12/1977 | Germany . |
| 3134050 | 3/1983 | Germany . |
| WO 88/08667 | 11/1988 | WIPO . |

OTHER PUBLICATIONS

F.P. Greenspan et al., "Peracetic Acid Aerosols", pp. 59–64.

L.J. Fischbach, "Renalin: Qualification As a Dialyzer Sterilant", pp. 15–19.

M. Baldry, "Peroxygen Biocides in the Food and Drink Industry", Biesterfled, pp. 1–2, 11–12, 12–13.

F. Dumler et al., "Effect of Dialyzer Reprocessing Methods on Complement Activation and Hemodialyzer–Related Symptons", Artificial Organs, 11 (2), pp. 128–131, 1987.

H. Bauer et al., "Experience with the Disinfectant Peroxyacetic Acid (PES) for Hemodialyzer Reuse", Trans–Am Soc. Artif. Intern. Organs, vol. 29, pp. 662–665, 1983.

H. Feldman, "Removing Deposits from Drinking Water Storage Vessels", Water, vol. 83, p. 303.

Von II. Briedigkelt et al., "Investigation Into the Disinfection of Hemodialysis Equipment", Zsohr. Urol. Bd. 70, pp. 705–711, 1977.

(List continued on next page.)

*Primary Examiner*—Robert J. Warden, Sr.
*Attorney, Agent, or Firm*—Young & Thompson

[57] ABSTRACT

The invention concerns a hygienic agent for use in hemodialysis. This hygienic agent based on peracetic acid has an aqueous solution containing 6 to 8 weight % hydrogen peroxide, 0.1 to 1 weight % peracetic acid and 2 to 10 weight % acetic acid. Application to the disinfection, sterilization of dialysis generators, dialyzers, hemofilters and hemodialyzers and circuits of water treatment for hemodialysis.

4 Claims, 1 Drawing Sheet

OTHER PUBLICATIONS

M. Sproeig et al., "Disinfection of Hemodialysis Systems with Peracetic Acid", Dtsch. Ges. wesen 27, pp. 1085–1089, 1972.

R. Giertler et al., "Further Investigations On the Disinfection of Artificial Kidneys With Peracetic Acid", Zschr. Urol. 66, pp. 689–694, 1973.

H. Wenchel et al., "Microbe Reproduction In Various Sections of A Dialyzer By Peracetic Acid Preparations", Hygiene & Medizin 12, pp. 197–202, 1987.

Seymore S. Block, "Disinfection, Sterilization, and Preservation", Third Edition, 1983, pp. 401–402.

A. Dauphin et al., "Hygiene Hospitaliere Pratique", Editions Medicales Internationales, 1988, pp. 208–231.

HYGIENIC AGENT FOR USE IN HEMODIALYSIS

CROSS-REFERENCE TO RELATED APPLICATIONS

This application is a division of application Ser. No. 08/389,971, filed Feb. 16, 1995, now U.S. Pat. No. 5,851,483 which is a continuation of Ser. No. 08/111,966, filed Aug. 26, 1993 now abandoned, which is a continuation of Ser. No. 07/653,972, filed Feb. 11, 1991 now abandoned, which is a continuation of Ser. No. 07/438,293, filed Nov. 20, 1989 now abandoned.

BACKGROUND OF INVENTION

(1) Field of the Invention

The present invention concerns a hygienic agent for use in hemodialysis.

(2) Description of Prior Art

The principle of the extra corporeal dialysis is based on the contact of the blood to be purified with a dialysate through a semi-permeable membrane. In order to obtain efficient exchanges, the blood and dialysate must be permanently renewed, since the speed of diffusion, or of dialysis, depends on the difference of concentrations between the blood and the dialysate. This is obtained by creating an extra-corporeal circulation.

Any dialysis chain comprises a generator, a dialyzer, a dialysate and a water circuit.

The generators enable to obtain the dialysate, the circulation of the blood and of the dialysate, and the controls of the parameters of dialysis.

The artificial kidney or dialyzer permits the elimination of water and of the waste produced by the body by contacting the blood with a liquid which is the dialysate or a dialysis bath. The blood and the dialysate are separated from one and other only by means of a thin artificial organic membrane, of cellophane, cuprophane, polysulfone, polypropylene, polyamide, polyacetate, copolymer of acrylonitrile . . . This membrane can be prepared in the form of plates, as compartments which are piled over one and other, or in the form of coils, as a single compartment which is spirally wounded about an axis or finally as capillaries consisting of an assembly of very fine hollow fibres.

Thus, there are three types of dialysis which are often delivered sterile for single use.

In the coiled kidneys, of the type where two sheets of dialysing membrane are spirally wound in a parallel fashion about an axis, the blood circulates inside the envelope defined by the two sheets of the membrane and the dialysate on the outside. The coiled kidney is actually the less utilized.

The plate kidneys are all disposed according to the same diagram corresponding to an assembly of 15 to 20 sheets of membrane mounted as an arrangement of plates in a sandwich type fashion, so as to provide inserted blood compartments and dialysate compartments. The blood circulates from top to bottom between the sheets while the dialysate circulates in opposite direction.

The hollow fibre kidney contains very little blood; it offers a very weak resistance to the flow of blood. Instead of sheets of membrane in roller or plate arrangement, the dialysing surface is formed in the case of thousands of tiny hollow fibres. The blood passes from top to bottom and the dialysate passes around in the other direction.

The dialysate is a mixture of water and electrolytes, and the concentration of the electrolytes in the dialysate is provided so that the composition of the electrolytes in the blood is normal at the end of the operation.

For hemodialysis uses, water should be very pure and chains of hemodialysis are generally provided with a water treatment consisting of softeners, demineralizers, osmosers, filters and a container for storing water. After the container for storing water where is found a utilisation circuit which feeds the dialysis generators.

Since the appearance of the extra-corporeal blood purifying techniques, there were always problems associated with the disinfection and tartar removal from the material used.

The dialyzers are often materials considered to be for single use. However, certain establishments reuse them under the responsibility of medical doctors. Now the chain of dialysis can very easily be contaminated and this is the reason why it must absolutely be disinfected on a regular basis.

Clinical reports indicate that important microbial proliferations in hemodialysis apparatuses can have serious effects on patients who are dialysed. More particularly, such phenomenons as bacteremia, hepatitis, fever, shivers, hypotension and shock have been observed.

Hot sterilization which would represent the ideal hygienic step is actually not feasible because of the numerous elements of the chain of dialysis which are unstable with respect to heat.

The addition of impervious filters placed immediately before the dialyzer is not completely satisfactory, since virus, mycoplasma and certain bacteria can pass through these filters.

In addition these physical methods of disinfection require a regular chemical disinfection of the other elements of the chain of dialysis.

In view of all the requirements that an appropriate disinfecting agent should meet, namely a large spectrum of activity for an active time which is as short as possible, cleaning and material preserving properties as well as a capacity to be easily rinsed under controlled conditions, only certain compounds can be considered.

The products used for disinfection are generally formaldehyde or sodium hypochlorite.

The water circuit can be regularly disinfected with formaldehyde or with sodium hypochlorite.

This operation is generally carried out once every six months since it is time consuming and requires that the operation of hemodialysis be stopped.

Sodium hypochlorite is used under more or less substantial dilutions depending on use, of the order of 50%, for the disinfection of generators.

Formaldehyde is also used under more or less substantial dilutions depending on the intended use.

These disinfecting products require multiple manipulations, such as preparations and dilutions and involved risks. Thus, formaldehyde can produce an allergy which is well classified as a professional disease. Sodium hypochlorite brings in chlorine in a highly pure medium, which represents an inconvenience.

Independently in the disinfection, various acids are used to remove tartar, such as acetic, lactic, citric acids . . .

Peracetic acid, whose disinfecting properties are known, has been proposed at a concentration of a few percentages, from the order of 3.5–4%, for the disinfection of generators of dialysis. Under this concentration, this type of disinfecting agent has various disadvantages, including the fact of being a product which presents risks for the treating staff because of its irritating effect on skin and mucous membranes, as well as its corrosive activity on the dialysis material.

Therefore, a search has been made for a new concept of hygienic agent for use in hemodialysis which would meet the following conditions: non-toxicity and biocompatibility in trace amounts, combined disinfection and tartar removal, active time lower than 30 minutes, complete disinfecting effect, easily rinsable and detectable, biodegradable, stable and ready to be used.

SUMMARY OF INVENTION

A hygienic agent for use in hemodialysis fulfilling all the above conditions has been found. In addition, this new formulation based on peracetic acid increases the properties of one of its active principles. It consists of an aqueous solution containing 6 to 8 weight % hydrogen peroxide, 0.1 to to 1 weight % peracetic acid and 2 to 10 weight % acetic acid.

An aqueous solution containing 6 to 8% hydrogen peroxide, 0.3 to 0.4% peracetic acid and 3.5 to 4.5% acetic acid is very advantageous, and in particular an aqueous solution containing 7% hydrogen peroxide, 0.35% peracetic acid and 3.5 to 4% acetic acid.

These aqueous solutions constituting a hygienic agent for use in hemodialysis are in the form of colorless, non-inflammable liquid which can be mixed with water in all proportions, does not foam, can easily be rinsed, can be kept at room temperature in its original wrapping, and has excellent stability for at least one year.

This hygienic agent for use in hemodialysis constitutes a harmless product under normal conditions of use, while permitting the disinfection and tartar removal from the hemodialysis material in a single operation, under the best conditions of hygiene and safety for the staff and the patients, in which no irritations nor allergies have been observed.

With a complete spectrum disinfecting formula, the new hygienic agent for use in hemodialysis has been shown to be an efficient bactericidal, fungicidal, sporicidal and virucidal agent. Because it is oxidizing and acidic, the hygienic agent for use in hemodialysis frees a particularly active oxygen. It reacts with the proteins of the membrane of the microorganisms and penetrates inside cells to destroy them. Its acidic character provides tartar removal properties.

The bactericidal activity of the hygienic agent for use in hemodialysis has been tested on hemodialysis material sequentially contaminated with the following germs: *Pseudomonas aeruginosa* and *Microbacterium smegmatis*. Depending on the dilutions used for the apparatuses, which consist of 3 to 10% aqueous solution containing 7% $H_2O_2$, 0.35% peracetic acid and 3.5% acetic acid, $10^6$ to $10^{10}$ bacteries/ml could be destroyed in 10 to 30 minutes.

The hygienic agent for use in hemodialysis was also tested in vitro according to the requirements of the AFNOR norms, and it is important to note that the disinfecting properties were maintained in the presence of organic materials (dialysate, blood, etc . . . ).

The fungicidal activity of the hygienic agent has been confirmed in vitro against yeasts and molds.

The sporicidic activity was tested in vitro and also on hemodialysis material contaminated with spores of *Bacillus cereus*. Depending on the apparatuses used, 3 to 10% of a solution of a hygienic agent containing 0.35% peracetic acid destroy $10^4$ to $10^6$ spores of Bacillus cereus in a period of 10 to 30 minutes.

The virucidal activity has been confirmed, such as on the AIDS virus. A contact of 30 minutes with a solution containing 0.35% peracetic acid at a concentration of 1.5% is sufficient to inactivate the HIV (Human Immunodeficiency Virus).

The hygienic agent according to the invention is not toxic for patients and staff. On the contrary, it has been observed that allergic and anaphylactic shocks have disappeared as well as a decrease of pyrogenic reactions, often found during dialysis.

The lethal dose LD 50 on rat was 1.540 mg/kg for peracetic acid, which corresponds to about 440 g/kg of a solution of hygienic agent containing 0.35% peracetic acid. The toxicity by acute inhalation: LC 50 is about 150 g/m$^3$ of the solution, the sub-acute toxicity corresponds to 20 g/m$^3$ and the tolerable threshold for the nose and the eyes is 0.3 g/m$^3$. The cutaneous toxicity, with respect to reversible lesions of the occular mucous membrane corresponds to the pure solution, the irritation threshold of the eye corresponds to a solution diluted one tenth. The irritating power on the skin is light with the pure solution and zero with a solution diluted to one tenth.

The hygienic agent for use in hemodialysis is biocompatible, and can be metabolized when present in traces. After 10,000 dialyses, no intolerance, irritation or allergy were observed among patients and treating staff. Tests made on blood of healthy donors have established that quantities lower than 0.2% solution of hygienic agent containing 0.35% peracetic acid are harmless and produce no modification of the erythrocytes (counts unchanged), hemoglobin, blood platelets, leukocytes and plasmic proteins. Thus, a concentration which is 150 times higher than the threshold of detection of the tests for rinsing control produced no ill effect on in vitro human blood.

The hygienic agent according to the invention finds applications in disinfection and tartar removal in all the stages of the cycle of dialysis.

It enables to disinfect and remove tartar from dialysis generators within less than one hour, including rinsing time. It can be used for a rapid disinfection between two dialysis treatments. Tartar removal from generators is realised simultaneously as their disinfection and there is no need to use another acid. Disinfection is carried out while the chemical disinfection cycle of the generators take place, and the periods of contact and rinsing are adjusted on the apparatuses, generally between 20 to 30 minutes of contact and 30 minutes of rinsing with osmotic water. For a normal chemical disinfection cycle it is recommended to use a dilution between $\frac{1}{10}$th and $\frac{1}{5}$sth, preferably $\frac{1}{30}$th.

The invention can also be used to make sure that generators awaiting utilisation in a dialysis cycle are kept sterile.

The hygienic agent according to the invention enables to disinfect water treatment circuits which are used for hemodialysis, in particular in the recirculation loop. This disinfecting agent can quite easily be used with short contact times, about 30 minutes, which enables to provide weekly or daily treatments according to needs. The agent can be used to disinfect channels, filters, and loops with a decrease of $10^6$ to $10^7$ germs/ml. Disinfection is followed by rinsing with osmotic water, during a short period of time of the order of 30 minutes to 2 hours depending on the circuits used.

The new peracetic acid-hydrogen peroxide-acetic acid composition can be used as the single cleaning and disinfection agent in the sterilisation of dialyzers, hemofilters, hemodialyzers. The possibility of reusing dialyzers treated with such composition constitutes a simple method which is very efficient, and well accepted by the treating staff. The composition ensures an average number of 8 to 12 reutilisation times for each dialyzer, under high bacteriological security conditions, thus permitting to consider the possibility of significantly reducing the total cost of the therapeutic treatment while enabling to use "highly permeable" membranes (better quality but very expensive).

The germicidal action of the disinfection agent extends for at least 15 days thus permitting an easy preservation of the modules of dialysis from one treatment to the other.

Under conditions of automated re-utilisation, the optimal dilution to strip the dialyzers as well as possible seem to be between 1/10th and 2/7th. In this case, the average reutilisation number is 8 to 9 with a single automated reconditionning of the modules of dialysis, with an apparatus for reutilisation ensuring a rinsing and cleaning of the high flow blood compartment in the direction of the fibres as well as by retrofiltration. The reutilisation of dialyzers with the recommended dilutions is never associated with a degradation of the filters or of the material to be reutilised.

DESCRIPTION OF PREFERRED EMBODIMENTS

Figure 1:
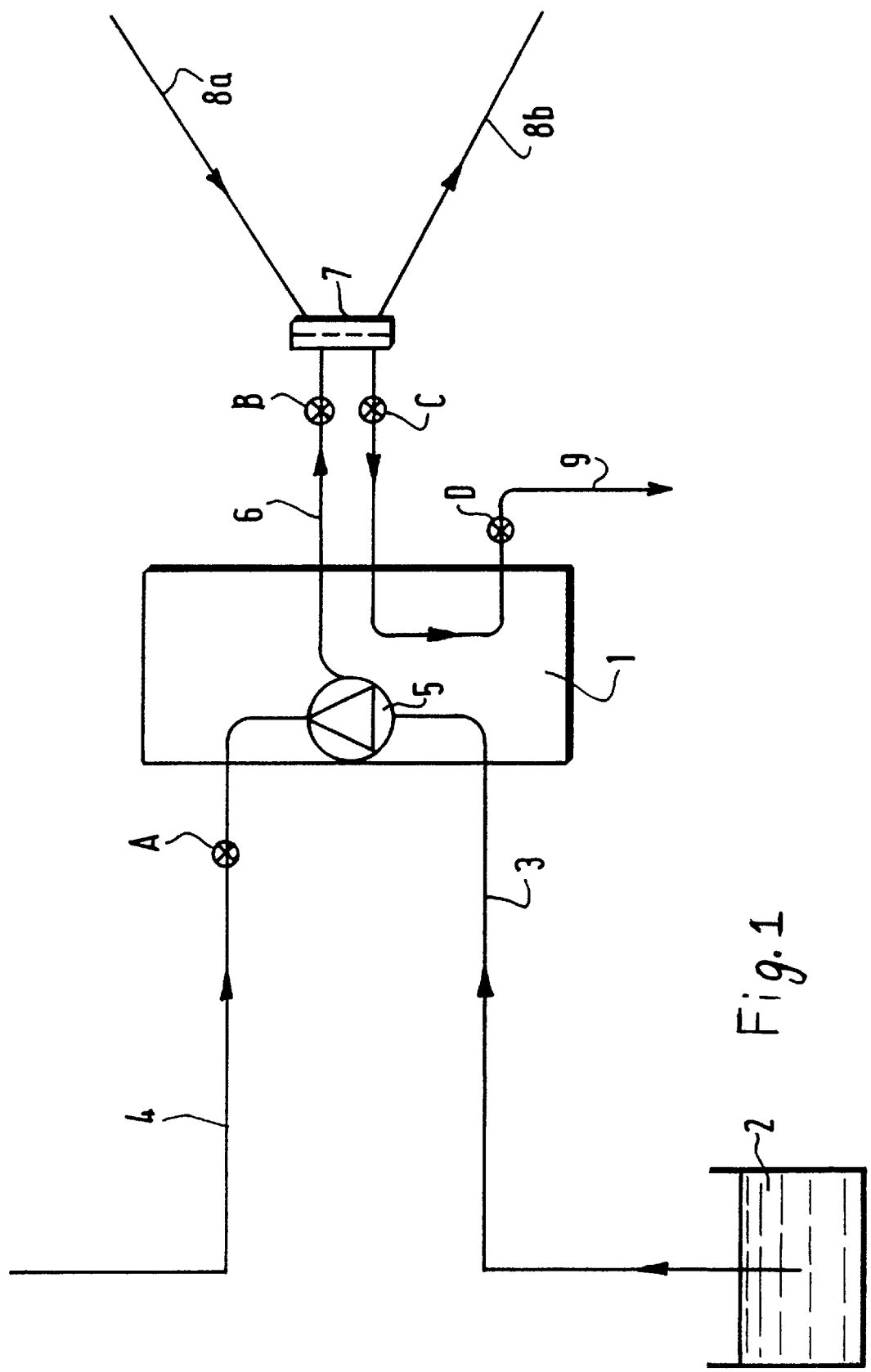
FIG. 1 is a schematic illustration of a chain dialysis used for carrying disinfection according to the invention.

Non-limiting examples of application of the hygienic agent according to the invention designated by Dialox® are given hereinafter.

EXAMPLE 1
Disinfection of generators of dialysis

The chain of dialysis in which the disinfection tests have been carried out, is represented in the annexed figure. This chain comprises generator (1) in which the preparation of the dialysis bath is carried out, from the dialysate sampled in the reservoir (2) and fed toward the generator by means of the circuit (3). Water circulates in the circuit (4) until reaching the generator, and the dilution of the dialysis bath is carried out by means of the measuring pump (5). The dialysis bath leaves the generator via circuit (6) to be introduced in the dialyzer (7), after exchange with the blood of the sick person according to circuit (8a), (8b), and the dialysis bath is sent to a drainage via circuit (9).

For this series of tests the generator is placed in position of disinfection, and the tests were carried out with various strains of germs which were purposely introduced in the circuit (3). The generator takes sample on the circuit (3) and automatically dilutes the hygienic agent Dialox® by means of the measuring pump (5).

These tests were carried out in various types of generators with different dilutions of Dialox® corresponding to a solution containing 0.35% peracetic acid, 7% $H_2O_2$ and 3.5% acetic acid and contact times between 10 to 30 minutes.

The samples were respectively taken at points (A) on the water circuit (4) before entering the generator, (B) on the circuit (6) of the dialysis bath before entering the dialyzer, (C) on the circuit of the dialysis bath (9) close to the outlet of the dialyzer, and at (D) before rejecting it to be drained. The introduction of the germs is controlled, as well as the samples carried with a series of probes, at the osmotic water inlet (A), inlet of kidney (B), outlet of kidney (C) and drainage outlet (D). In each case, the initial and final count and the decrease of the number of germs are given.

EXAMPLE 1a

Generator of the type Frénesius®.

TABLE Ia

| Site of sampling | Strain Dilution Time (T) of contact | | |
|---|---|---|---|
| | Initial count/ ml | Final count/ 50 ml | Decrease log 10 |
| Pseudomonas aeruginosa DIALOX ® 1/35th 20 Minutes (mn) | | | |
| A | 0 | 0 | 0.00 |
| B | 8.00E + 08 | 0 | 10.60 |
| C | 8.00E + 08 | 0 | 10.60 |
| D | 8.00E + 08 | 0 | 10.60 |
| Spores of Bacillus cereus DIALOX ® 1/35th 20 mn | | | |
| A | 0 | 0 | 0.00 |
| B | 3.00E + 06 | 0 | 8.18 |
| C | 3.00E + 06 | 0 | 8.18 |
| D | 6.00E + 06 | 0 | 8.48 |

EXAMPLE 1b

Generator of the type Mionitral (HOSPAL®)

TABLE Ib

| Site of sampling | Strain Dilution T. of contact | | |
|---|---|---|---|
| | Initial count/ ml | Final count/ 50 ml | Decrease log 10 |
| Pseudomonas aeruginosa DIALOX ® 1/35th 30 (mn) | | | |
| A | 0 | 0 | 0.00 |
| B | 1.00E + 06 | 0 | 7.70 |
| C | 1.00E + 06 | 0 | 7.70 |
| D | 1.00E + 07 | 0 | 8.70 |
| Mycobacterium smegmatis DIALOX ® 1/35th 30 mn | | | |
| A | 0 | 0 | 0.00 |
| B | 1.00E + 06 | 0 | 7.70 |
| C | 1.00E + 06 | 0 | 7.70 |
| D | 1.00E + 06 | 0 | 8.70 |
| Spores of Bacillus cereus DIALOX ® 1/35th 30 mn | | | |
| A | 0 | 0 | 0.00 |
| B | 4.00E + 06 | 0 | 8.30 |
| C | 4.00E + 06 | 0 | 8.30 |
| D | 7.00E + 06 | 0 | 8.54 |

EXAMPLE 1c
Generator of the type AK 10 (GAMBRO®)

TABLE IC

| Site of sampling | Initial count/ ml | Final count/ 50 ml | Decrease log 10 |
|---|---|---|---|
| Strain Dilution T. of contact | | | |
| Pseudomonas aeruginosa DIALOX ® 1/35th 20 (mn) | | | |
| A | 0 | 0 | 0.00 |
| B | 6.00E + 08 | 0 | 10.48 |
| C | 6.00E + 08 | 0 | 10.48 |
| D | 6.00E + 08 | 0 | 10.48 |
| Mycobacterium smegmatis DIALOX ® 1/35th 10 mn | | | |
| A | 0 | 0 | 0.00 |
| B | 1.00E + 07 | 0 | 8.70 |
| C | 1.00E + 07 | 0 | 8.70 |
| D | 9.00E + 07 | 0 | 9.65 |
| Spores of Bacillus cereus DIALOX ® 1/35th 10 mn | | | |
| A | 0 | 0 | 0.00 |
| B | 1.00E + 06 | 900 | 4.74 |
| C | 1.00E + 06 | 700 | 4.85 |
| D | 2.00E + 06 | 1000 | 5.00 |
| Spores of Bacillus cereus DIALOX ® 1/35th 10 mn | | | |
| A | 0 | 0 | 0.00 |
| B | 8.00E + 06 | 5000 | 4.90 |
| C | 8.00E + 06 | 4000 | 5.00 |
| D | 1.00E + 07 | 3000 | 5.22 |
| Spores of Bacillus cereus DIALOX ® 1/35th 10 mn | | | |
| A | 0 | 0 | 0.00 |
| B | 4.00E + 06 | 0 | 8.30 |
| C | 4.00E + 06 | 0 | 8.30 |
| D | 4.00E + 06 | 0 | 8.30 |

EXAMPLE 1d
Comparative test for the disinfection of a generator of the type AK 10 (GAMBRO®)

TABLE Id

| Site of sampling | Initial count/ ml | Final count/ 50 ml | Decrease log 10 |
|---|---|---|---|
| Strain Dilution T. of contact | | | |
| Spores of Bacillus cereus 4% formaldehyde 12 hours | | | |
| A | 0 | 0 | 0.00 |
| B | 1.00E + 06 | 300 | 5.22 |
| C | 1.00E + 06 | 500 | 5.00 |
| D | 1.00E + 06 | 150 | 5.52 |

EXAMPLE 2

Ex vivo study of the germicidal power of an aqueous solution containing 3.5% peracetic acid, 7% $H_2O_2$ and 3.5% acetic acid (Dialox®).

The germicidal power of the Dialox® has been studied in vitro on used hemodiafilters (HF 80, polysulfone membrane, Frésénius®) which were sequentially contaminated by 3 types of germs (*Pseudomonas aeruginosa, Mycobacterium smegmatis* and *Bacillus cereus* in sporulated form).

For each type of germ 5 hemodiafilters were used: the first was used as indicator of contamination and the four others were used as indicator of the efficiency of the disinfecting product. These hemodiafilters were submitted to the normal procedure for reutilisation with disinfection by passing through Renatron®, which is an apparatus for reutilisation ensuring a highly efficient rinsing and cleaning of the blood compartment in the direction of the fibres as well as by retrofiltration.

These times of contact of the membranes with the disinfecting solution were respectively 5, 10, 20 and 30 minutes, and the count of the colonies of germs collected on the membranes were carried out at the 24th, 48th, 72nd and 96th hour of culture period.

The bactericidal power of Dialox® expressed as a logarithmic reduction of the number of germs by ml obtained for the three categories of germs tested as a function of time, is represented in the following table.

TABLE II

| Time Minutes | Count A T = 0 | Count after contact time | Reduction LOG 10 |
|---|---|---|---|
| PSEUDOMONAS AEROGINOSA | | | |
| 5 | $1.2 \cdot 10^7$ g/ml | 0 | 7.08 |
| 10 | $1.2 \cdot 10^7$ g/ml | 0 | 7.08 |
| 15 | $1.2 \cdot 10^7$ g/ml | 0 | 7.08 |
| 20 | $1.2 \cdot 10^7$ g/ml | 0 | 7.08 |
| MYCOBACTERIUM SMEGMATIS | | | |
| 5 | $5.1 \cdot 10^7$ g/ml | 0 | 7.71 |
| 10 | $5.1 \cdot 10^7$ g/ml | 0 | 7.71 |
| 15 | $5.1 \cdot 10^7$ g/ml | 0 | 7.71 |
| 20 | $5.1 \cdot 10^7$ g/ml | 0 | 7.71 |
| BACILLUS CEREUS SPORULE | | | |
| 5 | $4.0 \cdot 10^7$ g/ml | 0 | 6.60 |
| 10 | $4.0 \cdot 10^7$ g/ml | 0 | 6.60 |
| 15 | $4.0 \cdot 10^7$ g/ml | 0 | 6.60 |
| 20 | $4.0 \cdot 10^7$ g/ml | 0 | 6.60 |

For a contaminating solution comprising $10^6$ to $10^7$ units forming colonies (U.F.C.)/ml, the reduction on the blood sector as well as on the dialysate sector is between 6 to 7 log after 5 minutes, of contact for a solution of Dialox® diluted 1/10th. The reduction is identical for germs which are sporulated or unsporulated. The bactericidal effect thus appears to be absolute for Dialox® diluted 1/10th after 5 minutes of contact.

EXAMPLE 3

In vivo study of the cleaning and disinfecting effect of Dialox® on the modules of dialysis.

This in vivo evaluation was carried out on ten patients in stable condition of chronic kidney insufficiency, for extra kidney assistance, by hemodialysis, hemofiltration or hemodiafiltration.

Three models of dialyzers were used: HF 80 (polysulfone membrane Frésénius®), Filtral 16 polyacrylonitrile AN69 HOSPAL®, FH 88 (polyamide membrane, GAMBRO®). 6 dialyzers have been used for each patient.

The reconditionning of the modules of dialysis was carried out automatically on a Renatron® as the treatment was terminated.

The cleaning agent was Dialox® at 0.35% peracetic acid. For cleaning filters, 2/7th, 1/7th, 1/10th, 1/20th dilutions were used. The dilution used for maintaining the filters sterile from one treatment to the other was 1/10th.

Table II indicates the average number of reutilization of 60 modules with 10 patients (represented by their initials) under 2 dilutions of Dialox® at 0.35% peracetic acid, respectively 1/20th and 2.7th.

TABLE III

Reaction of patient
Dilution of Dialox ®

| Patient Filter | BC FH88 | CJ FH88 | RY FH88 | FA HF80 | EK HF80 |
|---|---|---|---|---|---|
| 1/20th X | 7 | 8.2 | 5.3 | 4.3 | 9.5 |
| 2/7th X | 8.5 | 7.7 | 6.2 | 6.0 | 9.8 |
| | EA FH80 | EF HF80 | TR HF80 | DV F16 | FP F16 |
| 1/20th X | 9.7 | 9.8 | 9.2 | 7.7 | 11.2 |
| 2/7th X | 10 | 10.2 | 9.8 | 7.8 | 10.3 |

X: number of reutilisation average/patient.

The average number of reutilisation was therefore of 8 (at most 4 to 11 times) with a good possibility of reproduction on the same patient whatever the dilution of Dialox® used.

In Table IV there is represented the average number of reutilisation of the modules of dialysis depending on their mode of utilisation in hemodialysis (HD), in hemofiltration (FH) or in hemodiafiltration (HDF) under 4 different dilutions of Dialox® at 0.35% peracetic acid, respectively 1/20th, 1/10th, 1/7th and 2/7th.

TABLE IV

Influence of the method of dialysis

| Dilution of Dialox ® | HF | HDF | HD |
|---|---|---|---|
| 1/20th | | | |
| X | 6.2 | 9.5 | 9.4 |
| n | (18) | (30) | (12) |
| 1/10th | | | |
| X | 7.5 | 9 | 10.5 |
| n | (3) | (5) | (2) |
| 1/7th | | | |
| X | 7.1 | 10.0 | 9.1 |
| n | (18) | (30) | (12) |
| 2/7th | | | |
| X | 7.3 | 9.2 | 10.0 |
| n | (3) | (5) | (2) | n: total number of tests.
X: average number of reutilisation/method.

The influence of the method of dialysis is clear when comparing the 2 most representative groups, namely those corresponding to 1/20th and 1/7th dilutions. These data establish that the modules used in hemofiltration have an average number of reutilisation significantly lower than those used in hemodialysis or in hemodiafiltration.

The influence of the type of dialyzer was studied for the dialysis modules FH 88, HF 80 and FILTRAL 16 at 4 different dilutions of Dialox® 0.35% peracetic acid, respectively 1/20th, 1/10th, 1/7th and 2/7th.

The average number of reutilisation (x) by dialyzer is given in table V.

TABLE V

| Dilution of Dialox ® | Influence of the method of dialyzer | | |
|---|---|---|---|
| | HF88 | HF80 | F16 |
| 1/20th | | | |
| X | 5.2 | 7.1 | 6.3 |
| n | (30) | (50) | (20) |
| 1/10th | | | |
| X | 5.3 | 7.6 | 7.1 |
| n | (3) | (5) | (2) |
| 1/7th | | | |
| X | 5.7 | 7.7 | 6.2 |
| n | (30) | (50) | (20) |
| 2/7th | | | |
| X | 5.3 | 7.8 | 7.0 |
| n | (3) | (5) | (2) | n: total number of tests.
X: average number of reutilisation/dialyzer.

These data establish that there is a significant difference only between hemofilters FH88® and the group of hemodiafilters HF80® and FILTRAL 16®.

During this program of reutilisation of the module of dialysis no particular reaction was observed on the patients and the performances of the dialysis were not affected significantly by the reutilisation.

EXAMPLE 4

Disinfection of the water circuit.

In this type of disinfection, there was used a disinfecting agent containing 0.35% peracetic acid, Dialox®, at a dose of 5 liters for 100 liters of water injected in a buffer capacity. During disinfection, the circulation pumps of the circuit should operate to circulate the mixture of water and disinfecting agent. The circulation/disinfection time of contact is 30 minutes. Rinsing of the circuit is not carried out with osmotic water.

What is claimed is:

1. A method of disinfecting and removing tartar from interior portions of a dialysis generator, the method comprising the steps of:

introducing into the dialysis generator a sterilization composition consisting essentially of an aqueous solution of 6 to 8 percent by weight hydrogen peroxide, 0.1–1 percent by weight peracetic acid, and 2 to 4.5 percent by weight acetic acid, the composition remaining stable for at least a year;

adjusting the dialysis generator so that the sterilization composition is automatically diluted in water by the ratio of composition-to-water of 1:10 to 1:35 to provide a diluted composition and so that the diluted composition is placed in contact with the interior portions of the dialysis generator for a period of 20 to 30 minutes; and rinsing the contacted interior portions of the dialysis generator with osmotic water for a period of about 30 minutes.

2. A method of disinfecting and removing tartar from water treatment circuits of dialysis equipment, the method comprising the steps of:

diluting a sterilization composition which remains stable for at least a year and which consists essentially of an aqueous solution of 6 to 8 percent by weight hydrogen peroxide, 0.1–1 percent by weight peracetic acid, and 2 to 4.5 percent by weight acetic acid, in water by the ratio of composition-to-water of 1:10 to 1:35 to provide a diluted composition;

placing the diluted composition in contact with the water treatment circuits of the dialysis equipment for a period of about 30 minutes; and rinsing the contacted water treatment circuits with osmotic water for a period of 30 minutes to 2 hours.

3. A method of disinfecting and removing tartar from interior portions of dialyzers, hemofilters and hemodialyzers, the method comprising the steps of:

diluting a sterilization composition, which remains stable for at least a year and which consists essentially of an aqueous solution of 6 to 8 percent by weight hydrogen peroxide, 0.1–1 percent by weight peracetic acid, and 2 to 4.5 percent by weight acetic acid, in water by the ratio of composition-to-water of 1:10 to 2:7 to provide a diluted composition;

placing the diluted composition in contact with the interior portions of the dialyzers, hemofilters and hemodialyzers for a period of 20 to 30 minutes; and rinsing the contacted interior portions of the dialysis generator with osmotic water for a period of about 30 minutes.

4. A composition for disinfecting and removing tartar from dialysis equipment, consisting essentially of an aqueous solution of 6 to 8 percent by weight hydrogen peroxide, 0.1–1 percent peracetic acid, and 2 to 4.5 percent by weight acetic acid.

* * * * *